United States Patent
Fromentin et al.

(10) Patent No.: US 11,045,511 B2
(45) Date of Patent: Jun. 29, 2021

(54) COMPOSITIONS AND METHODS USEFUL IN TREATMENT OF LOWER URINARY TRACT SYMPTOMS, BENIGN PROSTATIC HYPERPLASIA, ERECTILE DYSFUNCTION AND OTHER DISEASES OR SYMPTOMS

(71) Applicant: Naturex Inc., South Hackensack, NJ (US)

(72) Inventors: Emilie Annie Claudie Fromentin, Brain sur L'authion (FR); Douglas Andrew Klaiber, Forestdale, MA (US); Daniel David Souza, East Sandwich, MA (US)

(73) Assignee: Naturex Inc., South Hackensack, NJ (US)

(*) Notice: Subject to any disclaimer, the term of this patent is extended or adjusted under 35 U.S.C. 154(b) by 0 days.

(21) Appl. No.: 15/979,265

(22) Filed: May 14, 2018

(65) Prior Publication Data
US 2018/0256663 A1    Sep. 13, 2018

Related U.S. Application Data

(63) Continuation of application No. 15/150,722, filed on May 10, 2016, now abandoned, which is a continuation of application No. PCT/US2014/064961, filed on Nov. 11, 2014.

(60) Provisional application No. 61/902,376, filed on Nov. 11, 2013.

(51) Int. Cl.
| | |
|---|---|
| A61K 36/45 | (2006.01) |
| A61K 9/48 | (2006.01) |
| A61K 9/00 | (2006.01) |
| A61K 9/16 | (2006.01) |
| A61K 9/20 | (2006.01) |
| A61K 31/09 | (2006.01) |
| A61K 31/192 | (2006.01) |
| A61K 31/216 | (2006.01) |
| A61K 31/34 | (2006.01) |
| A61K 31/341 | (2006.01) |
| A61K 31/352 | (2006.01) |
| A61K 31/353 | (2006.01) |
| A61K 31/7048 | (2006.01) |

(52) U.S. Cl.
CPC ............ *A61K 36/45* (2013.01); *A61K 9/0053* (2013.01); *A61K 9/16* (2013.01); *A61K 9/20* (2013.01); *A61K 9/48* (2013.01); *A61K 9/4875* (2013.01); *A61K 31/09* (2013.01); *A61K 31/192* (2013.01); *A61K 31/216* (2013.01); *A61K 31/34* (2013.01); *A61K 31/341* (2013.01); *A61K 31/352* (2013.01); *A61K 31/353* (2013.01); *A61K 31/7048* (2013.01)

(58) Field of Classification Search
CPC ...... A61K 36/45; A61K 31/09; A61K 31/192; A61K 31/216; A61K 31/34; A61K 31/341; A61K 31/352; A61K 31/353; A61K 31/7048; A61K 9/0053; A61K 9/16; A61K 9/20; A61K 9/48; A61K 9/4875; A61P 13/00; A61P 13/02; A61P 13/08; A61P 13/10; A61P 15/10
USPC ................................................. 424/732, 776
See application file for complete search history.

(56) References Cited

U.S. PATENT DOCUMENTS

| | | | |
|---|---|---|---|
| 5,525,341 A | 6/1996 | Walker et al. | |
| 6,391,345 B1 | 5/2002 | Heeg et al. | |
| 7,943,182 B2 | 5/2011 | Heeg et al. | |
| 8,557,305 B2 | 10/2013 | Ghaedian et al. | |
| 10,898,534 B2 * | 1/2021 | Fromentin | A61K 9/20 |
| 2001/0012525 A1 | 8/2001 | Mann | |
| 2004/0005308 A1 | 1/2004 | Kastke | |
| 2005/0186147 A1 | 8/2005 | Tamarkin et al. | |
| 2008/0199547 A1 * | 8/2008 | Heeg | A61K 8/922 424/732 |
| 2011/0064706 A1 | 3/2011 | Minatelli et al. | |
| 2011/0280971 A1 | 11/2011 | Heeg et al. | |
| 2013/0122151 A1 * | 5/2013 | Ghaedian | A23B 7/026 426/71 |

FOREIGN PATENT DOCUMENTS

| | | | | |
|---|---|---|---|---|
| FR | 2972328 A1 * | 9/2012 | ........... | A61K 31/592 |
| WO | 2011088420 A1 | 7/2011 | | |

OTHER PUBLICATIONS

L.N. Kuzminski, "Cranberry Juice and Urinary Tract Infections: Is There a Beneficial Relationship", Nutrition Reviews, vol. 54, No. 11. (Year: 1996).*
Kuzminski et al. Cranberry Juice and Urinary Tract Infections: Is There a Beneficial Relationship?L Nutrition Reviews, vol. 54, No. 11. (Year: 1996).*

(Continued)

*Primary Examiner* — Aaron J Kosar
(74) *Attorney, Agent, or Firm* — Curatolo Sidoti Co., LPA; Salvatore A. Sidoti

(57) ABSTRACT

The invention relates to therapeutic compositions, solid oral dosage forms, and methods for treating, preventing, or alleviating lower urinary tract symptoms (LUTS), benign prostatic hyperplasia (BPH), erectile dysfunction (ED), urinary incontinence, bladder obstruction, overactive bladder (OAB), underactive bladder, interstitial cystitis, prostatitis, bladder and prostate inflammation, prostate fibrosis or pelvic pain. The therapeutic compositions can comprise cranberry powder enriched in cranberry seeds or cranberry seed meal.

19 Claims, 2 Drawing Sheets

(56) References Cited

OTHER PUBLICATIONS

Figure 1:
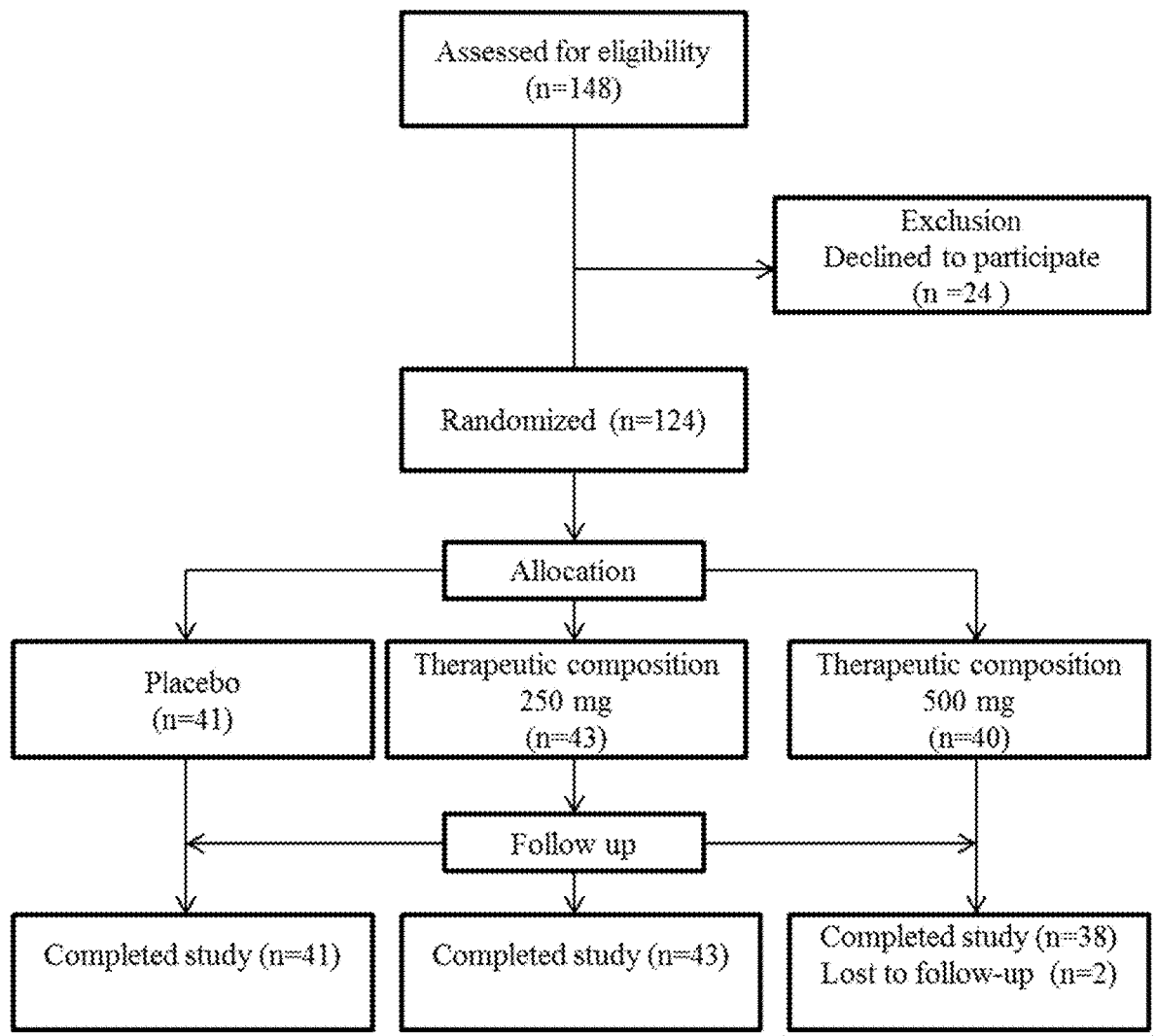

Vidlar et al. "The effectiveness of dried cranberries in men with Lower Urinary Tract Symptoms", British Journal of Nutrition, 2010, 104, 1181-1189. (Year: 2010).*
Cote, J., "PACran® Cranberry Powder: Beyond Urinary Tract Infection", NutraCos, vol. 11, No. 5, Sep. 1, 2012 (Sep. 1, 2012), pp. 43-46.
European Pharmacopoeia 5.0, "Hawthorn Berries" pp. 1712-1713; 2005:1220.
European Pharmacopoeia 6.0, "Hawthorn Berries" pp. 2034-2035, 2008:1220.
Hess, M.J., et al., "Evaluation of Cranberry Tablets for the Prevention of Urinary Tract Infections in Spinal Cord Injured Patients with Neurogenic Bladder", Spinal Cord, vol. 46, No. 9, Apr. 8, 2008 (Apr. 8, 2008), pp. 622-626.
Howell, A., et al., "Dosage Effect on Uropathogenic *Escherichia coli* Anti-Adhesion Activity in Urine Following Consumption of Cranberry Powder Standardized for Proanthocyanidin Content: A Multicentric Randomized Double Blind Study", BMC Infectious Diseases, Biomed Central, vol. 10, No. 1, Apr. 14, 2010 (Apr. 14, 2010), pp. 1-11.
International Search Report, PCT/US2014/064961, dated Jan. 21, 2015.
Pappas, E., et al., "Phytochemicals of Cranberries and Cranberry Products: Characterization, Potential Health Effects, and Processing Stability", Critical Reviews in Food Science and Nutrition, vol. 49, No. 9, Jan. 1, 2009 (Jan. 1, 2009), pp. 741-781.
Prior et al., "Multi-laboratory validation of a standard method for quantifying proanthocyanidins in cranberry poweders", J. Sci. Food Agric. 90:1473-8, 2010.
Protocol AOAC Official Method 986.13 "Quinic, Malic, and Citric Acids in Cranberry Juice Cocktail and Apple Juice", AOAC International 2005.
Protoc AOAC Official Method 977.20 "Separation of Sugars in Honey", AOAC International 2006.
Roehrborn, C.G., "Lower Urinary Tract Symptoms, Benign Prostatic Hyperplasia, Erectile Dysfunction, and Phosphodiesterase-5 Inhibitors", Review in Urology, vol. 6, No. 3, Mar. 23, 2004 (Mar. 23, 2004), pp. 121-127.
Sakakibara et al., "Simultaneous Determination of All Polyphenols in Vegetable, Fruits, and Teas", J. Agri. Food Chem., vol. 51:572-580, 2003.
Singelton et al., "Analysis of Total Phenols and other Oxidation Substrates and Antioxidants by Means of Folin-Ciocalteu Reagent", Methods in Enzymology, vol. 299:152-178, 1999.

Vidlar et al., "The effectiveness of dried cranberries {*Vaccinium macrocarpon*) in men with lower urinary tract symptoms", Brit. J. of Nutricion, vol. 104:1181-1189, 2010.
Zirk, M., et al., "Cranberry (*Vaccinium macrocarpon*) Proanthocyanidins and Their Effects on Urinary Tract Infections", Current Topics in Nutraceutical Research, vol. 2, No. 3, Jan. 1, 2004 (Jan. 1, 2004), pp. 153-160.
Drake, "Male lower urinary tract symptoms associated with overactive bladder", CUAJ 6(5Suppl2): S136-S137 (2012).
Forney et al., "Blueberry and cranberry fruit composition during development", Journal of Berry Research, 2: 169-177, (2012).
Kiosev, "Comprehensive reference of medicinal plants", Eksmo-Press, Moscow, pp. 693-694 (2001).
Lemack, "Defining the role of overactive bladder treatments in men with lower urinary tract symptoms", Nature Clinical Practice Urology, 4(4): 174-175 (2007).
Vostalova et al., "Are High Proanthocyanidins Key to Cranberry Efficacy in the Prevention of Recurrent Urinary Tract Infection?", Phytother. Res. 29: 1559-1567 (2015).
Upton et al., "Cranberry Fruit *Vaccinium macrocarpon* Aiton Revision, Standards of Analysis, Quality Control, and Therapeutics", American Herbal Pharmacopoeia and Therapeutic Compendium, pp. 1-94 (2016).
Colgan, R. et al., "Diagnosis and Treatment of Acute Uncomplicated Cystitis", American Family Physician, vol. 84, No. 7, Oct. 1, 2011, pp. 771-776.
Coyne, K. S. et al., "The Prevalence of Lower Urinary Track Symptoms (LUTS) and Overactive Bladder (OAB) by Racial/Ethnic Group and Age: Results from OAB-POLL", Neurourology and Urodynamics, vol. 32, (2013), pp. 230-237.
Roehrborn, C. G., Focus on Lower Urinary Track Symptoms: Nomenclature, Diagnosis, and Treatment Options, Highlights from the 5th International Consultation on Benign Prostatic Hyperplasia, Jun. 25-27, 2000, Paris, France, Reviews in Urology, vol. 3, No. 3, (2001), pp. 139-145.
Blumberg, J.B. et. al. "Cranberries and Their Bioactive Constituents in Human Health", Advances in Nutrition, vol. 4, No. 6, pp. 618-632, (2013).
Daniells, "Cranberry's benefits extend to prostates: Study", Nutra Ingredients usa.com, (2010).
Fellers, "Nutritive Value of Cranberries", American Journal of Public Health, vol. 23, No. 1, pp. 13-18, (1933).
Jensen et al, "Cranberry Juice and Combinations of Its Organic Acids Are Effective against Experimental Urinary Tract Infection", Frontiers in Microbiology, vol. 8, Article 542, (2017).
Wen et al., "Analysis of clinical characteristics of diseases related to lower urinary tract symptoms", Guangdong Medical Journal, vol. 34, No. 10, pp. 1556-1559, (2013).
Excerpt from the Ellura webpage as available on Oct. 16th, 2010, FAQ section; Annex 1, https://web.archive.org/web/20101017092713/http://www.myellura.com:80/about-ellura, (2010).

* cited by examiner

COMPOSITIONS AND METHODS USEFUL IN TREATMENT OF LOWER URINARY TRACT SYMPTOMS, BENIGN PROSTATIC HYPERPLASIA, ERECTILE DYSFUNCTION AND OTHER DISEASES OR SYMPTOMS

1. CROSS-REFERENCE TO RELATED APPLICATIONS

This application is a continuation of U.S. patent application Ser. No. 15/150,722, filed May 10, 2016, which is a continuation of, and claims the benefit of priority to International Application No. PCT/US2014/064961, filed Nov. 11, 2014, which claims the benefit of priority to U.S. Provisional Patent Application No. 61/902,376, filed Nov. 11, 2013, the entire disclosures of each of which are incorporated by reference herein, in their entirety.

2. FIELD

The present invention relates generally to treatment, prevention, and alleviation of lower urinary tract symptoms (LUTS), benign prostatic hyperplasia (BPH), erectile dysfunction (ED), urinary incontinence, and other diseases or symptoms.

3. BACKGROUND

Lower urinary tract symptoms (LUTS) become increasingly bothersome as men age, with a prevalence of moderate-to-severe symptoms rising to nearly 50% of men in their eighties. LUTS may or may not be related to benign prostatic hyperplasia (BPH), a histological condition characterized by the non-malignant overgrowth of prostatic tissue surrounding the urethra that occurs in 50% of men in their fifties and 90% of men in their eighties. LUTS can also arise from age-related bladder detrusor dysfunction and other sympathetic conditions. LUTS are further classified as voiding or storage symptoms and defined by the international prostate symptoms score (IPSS), a validated tool, widely used among the medical and scientific community.

Voiding symptoms include urinary hesitancy, delay in initiating micturition, intermittency, involuntary interruption of voiding, weak urinary stream, straining to void, a sensation of incomplete emptying, terminal dribbling, and may be caused by prostate enlargement or tissue inflammation. Storage symptoms can include urinary frequency, nocturia, urgency, incontinence and bladder pain or dysuria, and may be caused by bladder detrusor overactivity. Physiological markers associated with increased risk of BPH include high levels of testosterone, dihydrotestosterone, dehydroepiandrosterone and estradiol, insulin-like growth factors and inflammatory markers.

Although LUTS and LUTS due to BPH are not a life-threatening condition, the impact of LUTS on quality-of-life (QoL) can be significant and treatment is necessary in most cases to avoid complications. Risk factors include age, prostatic volume and peak urinary flow rate as well as lifestyle, dietary pattern, alcohol consumption, physical activity or genetic factors. Upon diagnosis, watchful waiting is recommended in approximately 34% of cases in the United States. Registered pharmacological treatments for LUTS may be responsible for a variety of side effects, thus necessitating development of new treatments.

According to the American Urological Association, patients with a mild degree of bother (IPSS<8) or patients with moderate to severe symptoms (IPSS≥8) who are not bothered by their LUTS may be managed with watchful waiting and lifestyle modification. If significant bothersome symptoms persist despite conservative measures, the initiation of medical management is indicated and in certain cases, surgery may be recommended.

The National Institutes of Health estimates that erectile dysfunction (ED) affects as many as 30 million men in the United States. Incidence increases with age: about 4% of men in their 50s and nearly 17% of men in their 60s experience a total inability to achieve an erection. The incidence jumps to 47% for men older than 75.

Benign prostatic hyperplasia (BPH) is a common problem among older men, and is responsible for considerable disability. The prevalence of histologically diagnosed prostatic hyperplasia increases from 8% in men aged 31 to 40, to 40 to 50% in men aged 51 to 60, to over 80% in men older than age 80.

Urinary incontinence is an underdiagnosed and underreported problem that increases with age. It affects 50-84% of the elderly in long-term care facilities. At any age is more than 2 times more common in females than in males.

Overactive bladder (OAB) is prevalent in 10 to 18% of the population, affecting men and women nearly equally. OAB has a negative impact on patient's quality of life. LUTS associated with OAB are responsible of significant social, psychological, occupational, domestic, and physical stigmas.

4. SUMMARY

The invention is based, in part, on the discovery that addition of cranberry seeds or cranberry seed meal to dried cranberry powder provides a therapeutic composition that is effective against lower urinary tract symptoms (LUTS) and other diseases or symptoms without the side effects of existing treatments.

In one aspect, the invention provides a therapeutic composition comprising dried cranberry powder and dried cranberry seeds.

In another aspect, the invention provides therapeutic composition comprising dried cranberry powder and cranberry seed meal.

In some embodiments, the cranberry is *Vaccinium macrocarpon*.

In some embodiments, the cranberry is *Vaccinium microcarpon*.

In some embodiments, the cranberry is *Vaccinium oxycoccus*.

In some embodiments, the cranberry seeds are present in an amount of about 5% to about 50% by weight of the dried cranberry powder.

In some embodiments, the cranberry seeds are present in an amount of about 15% to about 25% by weight of the dried cranberry powder.

In some embodiments, the cranberry seeds are present in an amount of about 20% by weight of the dried cranberry powder.

In some embodiments, the cranberry seed meal is present in an amount of about 5% to about 50% by weight of the dried cranberry powder.

In some embodiments, the cranberry seed meal is present in an amount of about 15% to about 25% by weight of the dried cranberry powder.

In some embodiments, the cranberry seed meal is present in an amount of about 20% by weight of the dried cranberry powder.

In some embodiments, the composition comprises less than about 12% of organic acids by weight.

In some embodiments, the composition comprises less than 10% of organic acids by weight.

In some embodiments, the composition comprises about 5% to about 8% of organic acids by weight.

In some embodiments, the composition comprises less than about 15% of sugars by weight.

In some embodiments, the composition comprises less than about 12% of sugars by weight.

In some embodiments, the composition comprises from about 1% to about 5% of quinic acid by weight.

In some embodiments, the composition comprises from about 2.2% to about 3.2% of quinic acid by weight.

In some embodiments, the composition comprises from about 0.4% to about 4% of malic acid by weight.

In some embodiments, the composition comprises from about 0.8% to about 1.8% of malic acid by weight.

In some embodiments, the composition comprises from about 1% to about 5% of citric acid by weight.

In some embodiments, composition comprises from about 1.8% to about 3.2% of citric acid by weight.

In some embodiments, the composition comprises: 0.5% to 5.0% proanthocyanidins, 0.05% to 1.5% quercetin, 0.001% to 0.1% quercetin-3-glucoside, 0.001% to 0.1% quercetin-3-rhamnoside, 0.001% to 0.1% quercetin-3-xyloside, 0.001% to 0.1% quercetin-3-arabinoside, 0.001% to 0.5% myricetin, 0.001% to 0.1% peonidin-3-galactoside, 0.001% to 0.1% peonidin-3-glucoside, 0.001% to 0.1% peonidin-3-arabinoside, 0.001% to 0.1% cyanidin-3-glucoside, 0.001% to 0.1% cyanidin-3-galactoside, 0.001% to 0.1% cyanidin-3-arabinoside, 0.001% to 0.1% protocatechuic acid 0.001% to 0.1% p-coumaric acid, 0.001% to 0.1% caffeoyl-glucoside, 0.001% to 0.1% coumaroyl-glucoside, 0.001% to 0.1% cafeic acid, 0.001% to 0.1% chlorogenic acid or 0.01 to 1.5% ursolic acid by weight.

In some embodiments, the composition comprises: 1.0% to 1.2% proanthocyanidins, 0.16% to 0.20% quercetin, 0.07% to 0.09% quercetin-3-glucoside, 0.03% to 0.04% quercetin-3-rhamnoside, 0.019% to 0.025% quercetin-3-xyloside, 0.025% to 0.035% quercetin-3-arabinoside, 0.010% to 0.014% myricetin, 0.022% to 0.030% peonidin-3-galactoside, 0.0025% to 0.0035% peonidin-3-glucoside, 0.010% to 0.020% peonidin-3-arabinoside, 0.0005% to 0.0015% cyanidin-3-glucoside, 0.015% to 0.030% cyanidin-3-galactoside, 0.010% to 0.025% cyanidin-3-arabinoside, 0.019% to 0.025% protocatechuic acid, 0.04% to 0.06% p-coumaric acid, 0.015% to 0.025% caffeoyl-glucoside, 0.005% to 0.015% coumaroyl-glucoside, 0.010% to 0.015% cafeic acid or 0.030% to 0.04% chlorogenic acid by weight.

In some embodiments, the composition comprises about: 1.1% proanthocyanidins, 0.18% quercetin, 0.083% quercetin-3-glucoside, 0.034% quercetin-3-rhamnoside, 0.022% quercetin-3-xyloside, 0.030% quercetin-3-arabinoside, 0.012% myricetin, 0.027% peonidin-3-galactoside, 0.003% peonidin-3-glucoside, 0.014% peonidin-3-arabinoside, 0.001% cyanidin-3-glucoside, 0.022% cyanidin-3-galactoside, 0.018% cyanidin-3-arabinoside, 0.022% protocatechuic acid, 0.052% p-coumaric acid, 0.021% caffeoyl-glucoside, 0.011% coumaroyl-glucoside, 0.014% cafeic acid, 0.034% chlorogenic acid or 0.92% ursolic acid by weight.

In some embodiments, the composition comprises 1 to 100 µg lariciresinol, 1 to 100 µg secoisolariciresinol or 1 to 100 µg/pinoresinol per 100 g of the composition by weight.

In some embodiments, the composition comprises about 51 µg lariciresinol, about 12 µg secoisolariciresinol or about 78 µg/pinoresinol per 100 g of the composition by weight.

In another aspect, the invention provides a solid oral dosage form comprising a therapeutic composition described above.

In some embodiments, the solid oral dosage is a tablet.

In other embodiments, the solid oral dosage is a capsule.

In some embodiments, the solid oral dosage is a softgel.

In some embodiments, the solid oral dosage comprises 100 mg to 500 mg of the therapeutic composition.

In some embodiments, the solid oral dosage comprises 250 mg of the therapeutic composition.

In some embodiments, the solid oral dosage comprises 500 mg of the therapeutic composition.

In another aspect, the invention provides a method for alleviating lower urinary tract symptoms (LUTS) in a subject comprising administering to the subject in need thereof an effective amount of the composition described above.

In another aspect, the invention provides a method for alleviating the symptoms of benign prostatic hyperplasia (BPH) in a subject comprising administering to the subject in need thereof an effective amount of the composition described above.

In another aspect, the invention provides a method for treating erectile dysfunction (ED) in a subject comprising administering to the subject in need thereof an effective amount of the composition described above.

In another aspect, the invention provides a method for treating urinary incontinence in a subject comprising administering to the subject in need thereof an effective amount of the composition described above.

In another aspect, the invention provides a method for treating overactive bladder (OAB) in a subject comprising administering to the subject in need thereof an effective amount of the composition described above.

In other aspects, the invention provides a method for treating bladder obstruction, interstitial cystitis, underactive bladder, prostatitis, bladder and prostate inflammation, prostate fibrosis or pelvic pain in a subject comprising administering to the subject in need thereof an effective amount of the composition described above.

In some embodiments, the subject is a human.

In some embodiments, the human is a male.

In some embodiments, the human is a female.

5. BRIEF DESCRIPTION OF THE DRAWINGS

The invention is described with reference to the following figures, which are presented for purposes of illustration only and which is not intending to be limiting of the invention.

FIG. 1 illustrates a CONSORT diagram of the 148 men attending the first screening visit in the LUTS study.

Figure 2:
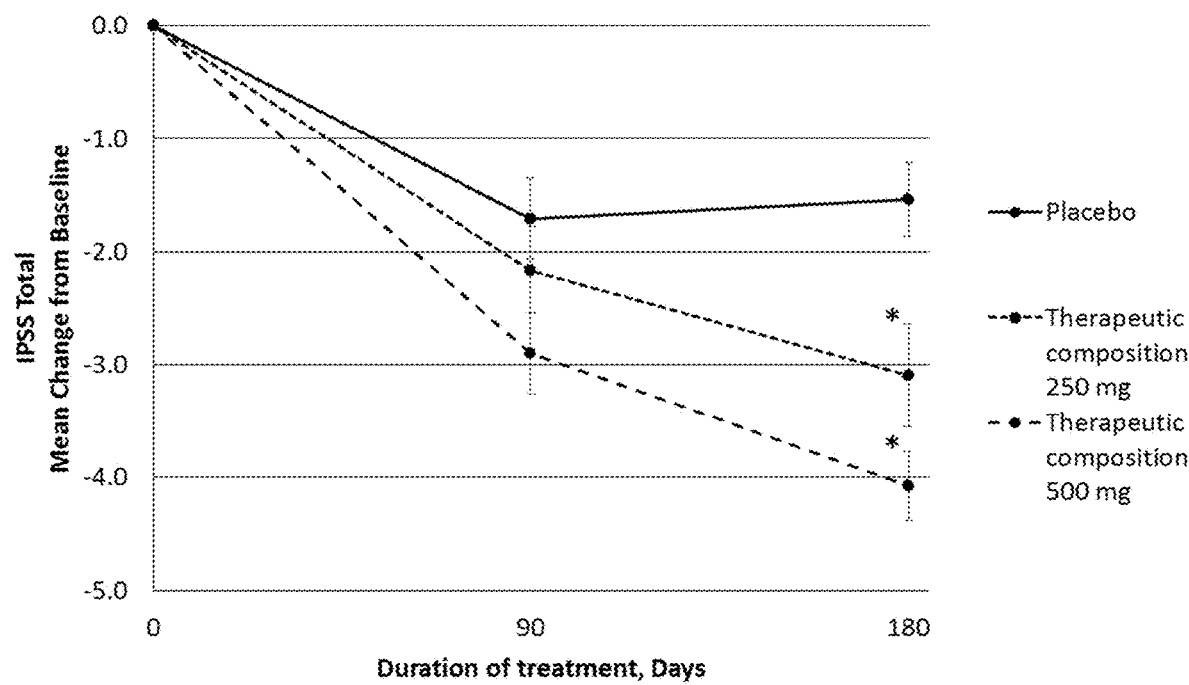

FIG. 2 illustrates a plot of the mean difference and corresponding 95% confidence interval in international prostate symptom scores (IPSS) at start, 3-months, and 6-months for the placebo group, the therapeutic composition 250 mg group, and the therapeutic composition 500 mg group in the LUTS study.

6. DETAILED DESCRIPTION

6.1 Definitions

The patent and scientific literature referred to herein establishes knowledge that is available to those of skill in the art. The issued U.S. patents, allowed applications, published foreign applications, and references that are cited herein are hereby incorporated by reference to the same extent as if each was specifically and individually indicated to be incorporated by reference.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values ≥0 and ≤2 if the variable is inherently continuous.

As used herein, unless specifically indicated otherwise, the word "or" is used in the inclusive sense of "and/or" and not the exclusive sense of "either/or."

As used herein, "about" means within ±10%. For example, "about 1" means "0.9 to 1.1", "about 2%" means "1.8% to 2.2%", "about 2% to 3%" means "1.8% to 3.3%", and "about 3% to about 4%" means "2.7% to 4.4%."

6.2 Cranberry Fruit

Cranberry fruit, e.g., *Vaccinium macrocarpon*, is recognized as a rich source of organic and phenolic acids, flavonols, flavan-3-ols, anthocyanins, proanthocyanidins (PACs) and pentacyclic triterpenoids, including ursolic and oleanolic acids.

A non-exhaustive list of pharmacoactive compounds that may be present in cranberry fruit is listed in Table 1.

TABLE 1

| | |
|---|---|
| Phenolic Acid Derivatives | Coumaroyl-hexose |
| | 6-Caffeoyl-D-glucose |
| | 3-caffeoylquinic acid (Chlorogenic acid) |
| | 4-hydroxybenzoic acid |
| | 3-hydroxybenzoic acid |
| | 5-p-hydroxybenzoic acid |
| | 6-p-hydroxybenzoic acid |
| | Gallic acid |
| | Benzoic acid |
| | Cinnamic acid |
| | dihydroxybenzoic acid |
| | o-hydroxycinnamic acid |
| | 4-hydroxy-3-methoxybenzoic acid (HVA) (vanillic acid) |
| | 3-hydroxyphenylacetic acid (3HPAA) |
| | 3-hydroxybenzoic acid (3HBA) |
| | 3,4-dihydroxybenzoic acid (3,4DHBA) (protocatechuic acid) |
| | 2,3-dihydroxybenzoic acid (2,3DHBA) (hypogallic acid) |
| | 2,4-dihydroxybenzoic acid (2,4DHBA) (b-resorcyclic acid) |
| | 2,5-dihydroxybenzoic acid (2,5DHBA) (genistic acid) |
| | 2,6-dihydroxybenzoic acid |
| | 3-hydroxycinnamic acid (3HCA) |
| | 4-hydroxycinnamic acid (4HCA) (p-coumaric acid) |
| | 4-hydroxy-3-methoxycinnamic acid (Ferulic acid) |
| | 3,4-dihydroxycinnamic acid (Caffeic acid) |
| | 3-hydroxyphenylpropionic acid (3HPPA) (phloretic acid) |
| | benzoylaminoacetic acid (hippuric acid) |
| | Salicylic acid |
| | Sinapic acid |
| | Ascorbic acid |
| | Ellagic acid |
| | Syringic acid |
| | Shikimic acid |
| | Ferruloyl glucoside |
| | 4-caffeoylquinic acid (Cryptochlorogenic acid) |

TABLE 1-continued

| | |
|---|---|
| Flavonols | Myricetin |
| | Quercetin |
| | Quercetin 3-galactoside |
| | Quercetin 3-glucoside |
| | Quercetin-3-rhamnoside |
| | Quercetin-3-xyloside |
| | Quercetin-3-arabinoside |
| | Quercetin glucuronide |
| | Myricetin-3-galactoside |
| | Myricetin-3-glucoside |
| | Isorhamnetin |
| Flavanols | (+)-catechin |
| | (−)-catechin |
| | Procyanidin A2 type isomer 1 |
| | Procyanidin A2 type isomer 2 |
| | Procyanidin A2 type isomer 3 |
| | (−)-epicatechin |
| | 3-methylcatechin |
| | 4-methylcatechin |
| | 3-methylepicatechin |
| | 4-methylepicatechin |
| Coumarins | Scopoletin |
| Anthocyanins | Cyanidin 3-galactoside |
| | Cyanidin 3-glucoside |
| | Peonidin 3-glucoside |
| | Cyanidin 3-arabinoside |
| | Peonidin 3-galactoside |
| | Peonidin 3-arabinoside |
| Chalcones | Phlorizin |
| Tocopherols | Alpha-tocopherol acetate |
| | Alpha-tocopherol |
| | Beta-tocopherol |
| | Gamma-tocopherol |
| | Delta-tocopherol |
| | Alpha-tocotrienol |
| | Beta-tocotrienol |
| | Gamma-tocotrienol |
| | Delta-tocotrienol |
| | Vitamin E |
| Sterols | Cholesterol |
| | Brassicasterol |
| | 24 methyl-cholesterol |
| | Campestanol |
| | Campesterol |
| | Delta-7-campesterol |
| | Delta-5,23 stigmastadienol |
| | Clerosterol |
| | Beta-sitosterol |
| | Sitostanol |
| | Delta-5-avenasterol |
| | Delta-5,24-stigmastadienol |
| | Delta-7-stigmasterol |
| | Delta-7-avenasterol |
| Fatty acids | Myristic acid |
| | Palmitic acid |
| | Palmitoleic acid |
| | Margaric acid |
| | Stearic acid |
| | Oleic acid |
| | Linoleic acid |
| | Linolenic acid |
| | Arachidic acid |
| | Gondoic acid |
| | Behenic acid |
| | Erucic acid |
| | Lignoceric acid |
| | Nervonic acid |
| Lignans | Syringaresinol |
| | Lariciresinol |
| | Medioresinol |
| | Lariciresinol-sesquilignan |
| | Secoisolariciresinol |
| | Pinoresinol |
| | Secoisolariciresinol-cyclolariciresinol |
| | 7-hydroxymatairesinol |
| | Nortrachelogenin |
| | 7-oxo-matairesinol |
| | Matairesinol |
| | α-conidendrin |

6.3 Therapeutic Compositions Based on Cranberry Fruit Components

Therapeutic compositions described herein can include one or more components described below in the ranges provided below.

In some embodiments, therapeutic compositions described herein comprise dried cranberry powder and dried cranberry seeds. In other embodiments, the therapeutic compositions described herein comprise dried cranberry powder and cranberry seed meal. The cranberry species used to make the compositions can be *Vaccinium macrocarpon*, *Vaccinium microcarpon*, or *Vaccinium oxycoccus*. However, other species of cranberries can also be used to make the compositions described herein.

Cranberry seeds can be present in the therapeutic composition in an amount of about 5% to about 50%, about 15% to about 25%, or about 20% by weight of the dried cranberry powder. Cranberry seed meal can be present in the therapeutic composition in an amount of about 5% to about 50%, about 15% to about 25%, or about 20% by weight of the dried cranberry powder.

A therapeutic composition can comprise less than about 12%, less than about 10%, or about 5% to about 8% of organic acids by weight. Exemplary organic acids include, but are not limited to, quinic acid, malic acid, and citric acid.

The organic acid content can be determined using the following modification of protocol AOAC 986.13 entitled *Quinic, Malic and Citric Acids in Cranberry Juice Cocktail and Apple Juice* (available from AOAC International, www.aoac.org). The analytical column is a C18 reverse phase column with a 5 µm particle size, 25 cm×4.6 mm in tandem with and followed by C18 reverse phase cartridges, with a 5 µm particle size and 10 cm long. Phosphate buffer, 0.2M $KH_2PO_4$, pH 2.4 is used. The flow rate is 0.80 mL/min, the analysis is performed at ambient temperature, and the detection wavelength is 214 nm. A dilution of the test agent can be performed in the mobile phase. CAS # for the standard are as follows: CAS-77-92-9 (citric acid), CAS-6915-15-7 (malic acid), CAS-77-95-2 (quinic acid). The formula used to calculate the concentration of each organic acid is as follows: (PA/PA')×(V'/V)×C, where PA and PA'=peak area of test solution and standard, respectively; V and V'=volume of test solution and standard, respectively; and C=concentration of standard, %. Shikimic acid and ascorbic acids can also be detected with this method.

A therapeutic composition can comprise from about 1% to about 5% or from about 2.2% to about 3.2% of quinic acid by weight.

A therapeutic composition can comprise from about 0.4% to about 4% or from about 0.8% to about 1.8% of malic acid by weight.

A therapeutic composition can comprise from about 1% to about 5% or from about 1.8% to about 3.2% of citric acid by weight.

A therapeutic composition can comprise less than about 15% or less than about 12% of sugars by weight. Fructose, glucose and sucrose are examples of sugars typically found in cranberry. The sugar content reflects the global sugar amount and individual breakdown was not provided on these lots.

The sugar content can be determined by HPLC, using the following modification of protocol AOAC 977.20. The column used is µ-Bondapak/Carbohydrate (Waters Associates, No. 84038) with a guard column or equivalent. The mobile phase consists of non-spectro acetonitrile diluted with water (83/17, v/v). The sugar standard solution consists of fructose (CAS #57-48-7), glucose (CAS #50-99-7) and sucrose (CAS #57-50-1). The sample is diluted in water and filtered through a 45 µm filter. 10 µL of sample are injected to the column at room temperature. The flow rate is 1.0 mL/min under isocratic conditions for 20 min. A refractive index detector is used. The amount of glucose, fructose, and sucrose is calculated from integrator values or from peak heights as follows: Weight % sugar=100×(PH/PH')×(V/V')×(W'/W) where PH and PH'=peak heights (or integrator values) of sample and standard, respectively; V and V'=mL sample and standard (50 and 100) solutions, respectively; and W and W'=g sample (5.000) and standard, respectively.

In some embodiments, the therapeutic composition comprises: 0.5% to 5.0% proanthocyanidins, 0.05% to 1.5% quercetin, 0.001% to 0.1% quercetin-3-glucoside, 0.001% to 0.1% quercetin-3-rhamnoside, 0.001% to 0.1% quercetin-3-xyloside, 0.001% to 0.1% quercetin-3-arabinoside, 0.001% to 0.5% myricetin, 0.001% to 0.1% peonidin-3-galactoside, 0.001% to 0.1% peonidin-3-glucoside, 0.001% to 0.1% peonidin-3-arabinoside, 0.001% to 0.1% cyanidin-3-glucoside, 0.001% to 0.1% cyanidin-3-galactoside, 0.001% to 0.1% cyanidin-3-arabinoside, 0.001% to 0.1% protocatechuic acid, 0.001% to 0.1% p-coumaric acid, 0.001% to 0.1% caffeoyl-glucoside, 0.001% to 0.1% coumaroyl-glucoside, 0.001% to 0.1% cafeic acid, 0.001% to 0.1% chlorogenic acid or 0.01 to 1.5% ursolic acid by weight.

The content of proanthocyanidins and one or more other components can be determined by HPLC-fluorescence using a Develosil Diol column or equivalent as follows. The column compartment is maintained at 35° C. The solvents used are as follows: (A) 2% acetic acid in acetonitrile and (B) is 95:3:2 methanol/water/acetic acid. A linear gradient is used from 0% to 40% B, in 35 min; 40% to 100% B, in 40 min; 100% isocratic B, in 45 min; and 100% to 0% B, in 50 min.

The content of anthocyanins (peonidin-3-galactoside, peonidin-3-glucoside, peonidin-3-arabinoside, cyanidin-3-glucoside, cyanidin-3-galactoside, cyanidin-3-arabinoside) can be determined by HPLC-UV at a wavelength of 535 nm. The column is Synergi Hydro-RP or equivalent. The column compartment is maintained at room temperature. The mobile phase A consists of an aqueous 5% formic acid solution and mobile phase B of methanol. The gradient applied is 0-2 min, 5% B; 2-10 min, 5-20% B; 10-15 min, 20% B; 15-30 min, 20-25% B; 30-35 min, 25% B; 35-50 min, 25-33% B; 50-55 min, 33% B; 55-65 min, 33-36% B; 65-70 min, 36-45% B; 70-75 min, 45-53% B; 75-80 min, 53-55% B; 80-84 min, 55-70% B; 84-88 min, 70-5% B; 88-90 min, 5% B.

The content of certain other phenolics can be determined by UPLC-MS/MS using the following method. An Acquity T3 column (Waters Associates) or equivalent is used and placed in the UPLC column compartment maintained at a temperature of 30° C. The solvents used are 0.1% Formic acid (A) and acetonitrile (B). A linear gradient is applied from 5% B; 0-4.5 min, 5-20% B; 4.5-6.45 min, isocratic 20% B; 6.45-13.5 min, 20-45% B; 13.5-16.5 min 45-100% B; 16.5-19.5 min isocratic 100% B; 19.5-19.52 min 100-5% B; 19.52-22.5 min. The detection is done by MS/MS and all standard compounds are tuned individually.

In some embodiments, the therapeutic composition comprises: 1.0% to 1.2% proanthocyanidins, 0.16% to 0.20% quercetin, 0.07% to 0.09% quercetin-3-glucoside, 0.03% to 0.04% quercetin-3-rhamnoside, 0.019% to 0.025% quercetin-3-xyloside, 0.025% to 0.035% quercetin-3-arabinoside, 0.010% to 0.014% myricetin, 0.022% to 0.030% peonidin-3-galactoside, 0.0025% to 0.0035% peonidin-3-glucoside, 0.010% to 0.020% peonidin-3-arabinoside, 0.0005% to 0.0015% cyanidin-3-glucoside, 0.015% to 0.030% cyanidin-3-galactoside, 0.010% to 0.025% cyanidin-3-arabinoside, 0.019% to 0.025% protocatechuic acid, 0.04% to 0.06% p-coumaric acid, 0.015% to 0.025% caffeoyl-glucoside, 0.005% to 0.015% coumaroyl-glucoside, 0.010% to 0.015% cafeic acid or 0.030% to 0.04% chlorogenic acid by weight.

In some embodiments, the therapeutic composition comprises about: 1.1% proanthocyanidins, 0.18% quercetin, 0.083% quercetin-3-glucoside, 0.034% quercetin-3-rhamnoside, 0.022% quercetin-3-xyloside, 0.030% quercetin-3-arabinoside, 0.012% myricetin, 0.027% peonidin-3-galactoside, 0.003% peonidin-3-glucoside, 0.014% peonidin-3-arabinoside, 0.001% cyanidin-3-glucoside, 0.022% cyanidin-3-galactoside, 0.018% cyanidin-3-arabinoside, 0.022% protocatechuic acid, 0.052% p-coumaric acid, 0.021% caffeoyl-glucoside, 0.011% coumaroyl-glucoside, 0.014% cafeic acid, 0.034% chlorogenic acid or 0.92% ursolic acid by weight.

In some embodiments, the therapeutic composition comprises 1 to 100 μg or about 51 μg lariciresinol per 100 g of the composition. In some embodiments, the therapeutic composition comprises 1 to 100 μg or about 12 μg secoisolariciresinol per 100 g of the composition. In some embodiments, the therapeutic composition comprises 1 to 100 μg or about 78 μg pinoresinol per 100 g of the composition.

The content of lignans can be determined by UPLC-MS/MS using an ACQUITY BEH C18 reverse phase column or equivalent as follows. The column compartment is maintained at 30° C. The solvents used are (A) Formic acid 0.1% and (B) Acetonitrile. The gradient is 5% B, 8.0 min, 30% B, 9.0 min, 30% B, 10.0 min, 50% B, 12.0 min, 50% B, 15.0 min, 95% B, 17.0 min 95% B, 17.5 min, 5% B, 23.0 min, 5% B. The detection is done by MS/MS and all standard compounds are tuned individually.

In some embodiments, the therapeutic compositions described above can be produced without cranberry fruit, e.g., by combining ingredients obtained from natural sources or by chemical synthesis into a therapeutic composition.

6.4 Solid Dosage Forms and Methods of Use

In some embodiments, a solid oral dosage comprising the therapeutic composition described herein is a tablet, a capsule, or a softgel. In some embodiments, such solid oral dosage comprises from 50 mg to 500 mg of the therapeutic composition, e.g., 50 mg, 100 mg, 150 mg, 200 mg, 250 mg, 300 mg, 350 mg, 400 mg, 450 mg or 500 mg.

Solid dosage forms comprising the therapeutic compositions described herein optionally comprise a suitable amount of one or more pharmaceutically acceptable excipients so as to provide the form for proper administration to the subject.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present therapeutic compositions, if desired, can also contain minor amounts of wetting or emulsifying agents, or pH buffering agents. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995).

In some embodiments, a therapeutic composition described herein is formulated in accordance with routine procedures as a composition adapted for oral administration to human beings. Compositions for oral delivery can be in the form of tablets, lozenges, aqueous or oily suspensions, granules, powders, emulsions, capsules, softgels, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active therapeutic composition is also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be useful. Oral compositions can include standard excipients such as mannitol, lactose, starch, maltodextrin, cyclodextrins, alginate, arabic or guar gum, magnesium stearate, sodium saccharin, cellulose, and magnesium carbonate. In one embodiment, the excipients are of pharmaceutical grade.

Pharmaceutical dosage forms for oral use can be obtained through combination of a therapeutic composition described herein with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. Maltodextrin and cyclodextrins can also be used. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Softgels for oral use may consist of a gelatin based shell surrounding a liquid fill. Softgel shells can be made of a combination of gelatin, water, opacifier and a plasticiser such as glycerin and/or sorbitol.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Therapeutic compositions described herein can be administered by controlled-release or sustained release means or by delivery devices that are well known to those of ordinary skill in the art. Examples include, but are not limited to, those described in U.S. Pat. Nos. 5,674,533; 5,059,595; 5,120,548; 5,073,543; 5,639,476 and 5,354,556, each of which is incorporated herein by reference in its entirety. Such dosage forms can be useful for providing controlled or sustained release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled or sustained release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled or sustained release.

In some embodiments, a controlled or sustained release composition comprises a minimal amount of a therapeutic composition to alleviate the symptoms of, treat or prevent lower urinary tract symptoms (LUTS), benign prostatic hyperplasia (BPH), erectile dysfunction (ED), urinary incontinence, bladder obstruction, interstitial cystitis, overactive bladder (OAB), underactive bladder, prostatitis, bladder and prostate inflammation, prostate fibrosis or pelvic pain in a patient over a period of time. Advantages of controlled or sustained release compositions include extended activity of the drug, reduced dosage frequency, and increased subject compliance. In addition, controlled or sustained release compositions can favorably affect the time of onset of action or other characteristics, such as blood levels active ingredients present in the therapeutic composition, and can thus reduce the occurrence of adverse side effects.

Controlled or sustained release compositions can initially release an amount of an active ingredient present in the therapeutic composition that promptly produces the desired therapeutic or prophylactic effect, and gradually and continually release other amounts of the active ingredients present in the therapeutic composition to maintain this level of therapeutic or prophylactic effect over an extended period of time. To maintain a constant level of an active ingredient present in the therapeutic composition in the body, active ingredients present in the therapeutic composition thereof can be released from the dosage form at a rate that will replace the amount of the active ingredients present in the therapeutic composition being metabolized and excreted from the body. Controlled or sustained release of an active ingredient can be stimulated by various conditions, including but not limited to, changes in pH, changes in temperature, concentration or availability of enzymes, concentration or availability of water, or other physiological conditions or compounds.

The amount of a therapeutic composition that is effective in alleviating the symptoms of, treating or preventing lower urinary tract symptoms (LUTS), benign prostatic hyperplasia (BPH), erectile dysfunction (ED), urinary incontinence, bladder obstruction, interstitial cystitis, overactive bladder (OAB), underactive bladder, prostatitis, bladder and prostate inflammation, prostate fibrosis or pelvic pain can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of the practitioner and each subject's circumstances in view of, e.g., published clinical studies. Suitable effective dosage amounts, however, range from about 1 mg to about 5 grams about every 24 hours, although they are typically about 500 mg or less per every 24 hours. In one embodiment, the effective dosage is about 50 mg, about 100 mg, about 150 mg, about 200 mg, about 250 mg, about 300 mg, about 350 mg about 400 mg, about 450 mg about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 24 hours. Equivalent dosages can be administered over various time periods including, but not limited to, about every 2 hours, about every 4 hours, about every 6 hours, about every 8 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one therapeutic composition is administered, the effective dosage amounts correspond to the total amount administered.

The therapeutic composition can be administered as long as the symptoms persist or longer. In some embodiments, the therapeutic composition is administered for 3, 4, 5, 6, 7, 8, 9, 10, 11, 12, 13 or 14 days.

The dosage regimen utilizing the therapeutic compositions described herein can be selected in accordance with a variety of factors including type, species, age, weight, sex and medical condition of the subject; the severity of the condition to be treated; the route of administration; and the renal or hepatic function of the subject.

A therapeutic composition described herein can be administered in a single daily dose, or the total daily dosage can be administered in divided doses of two, three or four times daily.

The therapeutic composition described herein can be assayed in vitro or in vivo for the desired therapeutic or prophylactic activity prior to use in humans. Animal model systems can be used to demonstrate safety and efficacy.

5. Kits

Described herein are kits that can simplify the administration of a therapeutic composition described herein to a subject. A typical kit comprises a unit dosage form of a therapeutic composition described herein and a label or printed instructions. In some embodiments, the label or printed instructions instruct the use of the unit dosage form to alleviate the symptoms of, treat or prevent lower urinary tract symptoms (LUTS), benign prostatic hyperplasia (BPH), erectile dysfunction (ED), urinary incontinence, bladder obstruction, interstitial cystitis, overactive bladder (OAB), underactive bladder, prostatitis, bladder and prostate inflammation, prostate fibrosis or pelvic pain.

The kit can also further comprise a unit dosage form of another prophylactic or therapeutic agent. Examples of other prophylactic or therapeutic agents include, but are not limited to, those listed above.

6.4 Methods of Making Therapeutic Compositions

Therapeutic compositions described herein can be made as follows. Cranberry berries, skins, juice or pomace are weighed and mixed to create a slurry. If the composition is enriched in cranberry seeds, seeds are added to the slurry. Water is added to the slurry to reach about 5%-15% of the solids by weight. The slurry is passed through a 14 mesh screen, a shear pump, spray-dried and milled. If the therapeutic composition is enriched in cranberry seed meal, it is added during the milling. The milled composition is passed through a sieve, sealed and pelletized.

6.5 Methods of Using Therapeutic Compositions

6.5.1 Use in the Treatment of Lower Urinary Tract Symptoms (LUTS)

Therapeutic compositions described herein are useful for alleviating the symptoms of, treating or preventing lower urinary tract symptoms (LUTS). Accordingly, described herein are methods for alleviating, treating or preventing lower urinary tract symptoms (LUTS) in a subject comprising administering to the subject in need thereof an effective amount of a therapeutic composition described herein. LUTS may or may not be related to benign prostatic hyperplasia (BPH), a histological condition characterized by the non-malignant overgrowth of prostatic tissue surrounding the urethra. The alleviation of symptoms can be manifested by comparison to the same subject prior to administration or treatment with the therapeutic composition. The subject can be a human, for example a male or a female. In some embodiments, the human is older than 45 years, older than 50 years, older than 55 years, older than 60 years, older than 65 years, older than 70 years, older than 75 years or older than 80 years.

6.5.2 Use in the Treatment of Benign Prostatic Hyperplasia (BPH)

Benign prostatic hyperplasia (BPH), a histological condition characterized by the non-malignant overgrowth of prostatic tissue surrounding the urethra.

The therapeutic compositions described herein are useful for alleviating the symptoms of, treating or preventing to benign prostatic hyperplasia (BPH). Accordingly, described herein are methods for alleviating the symptoms of, treating or preventing benign prostatic hyperplasia (BPH) in a subject comprising administering to the subject in need thereof an effective amount of a therapeutic composition described herein. The alleviation of symptoms of benign prostatic hyperplasia (BPH) can be manifested by comparison to the same subject prior to administration or treatment with the therapeutic composition. The subject can be a human, for example a male. In some embodiments, the human is older than 45 years, older than 50 years, older than 55 years, older than 60 years, older than 65 years, older than 70 years, older than 75 years or older than 80 years.

6.5.3 Use in the Treatment of Erectile Dysfunction (ED)

The therapeutic compositions described herein are useful for alleviating the symptoms of, treating or preventing benign erectile dysfunction (ED). Accordingly, described herein are methods for alleviating the symptoms of, treating or preventing erectile dysfunction (ED) in a subject comprising administering to the subject in need thereof an effective amount of a therapeutic composition described herein. The alleviation of symptoms of erectile dysfunction (ED) can be manifested by comparison to the same subject prior to administration or treatment with the therapeutic composition. The subject can be a human, for example a male. In some embodiments, the human is older than 45 years, older than 50 years, older than 55 years, older than 60 years, older than 65 years, older than 70 years, older than 75 years or older than 80 years.

6.5.4 Use in the Treatment of Urinary Incontinence

The therapeutic compositions described herein are useful for alleviating the symptoms of, treating or preventing urinary incontinence. Accordingly, described herein are methods for alleviating the symptoms of, treating or preventing urinary incontinence in a subject comprising administering to the subject in need thereof an effective amount of a therapeutic composition described herein. The alleviation of symptoms of urinary incontinence can be manifested by comparison to the same subject prior to administration or treatment with the therapeutic composition. The subject can be a human, for example a male or a female. In some embodiments, the human is older than 45 years, older than 50 years, older than 55 years, older than 60 years, older than 65 years, older than 70 years, older than 75 years or older than 80 years.

6.5.5 Use in the Treatment of Overactive Bladder (OAB)

The therapeutic compositions described herein are useful for alleviating the symptoms of, treating or preventing overactive bladder (OAB). Accordingly, described herein are methods for alleviating the symptoms of, treating or preventing overactive bladder in a subject comprising administering to the subject in need thereof an effective amount of a therapeutic composition described herein. The alleviation of symptoms of overactive bladder (OAB) can be manifested by comparison to the same subject prior to administration or treatment with the therapeutic composition. The subject can be a human, for example a male or a female. In some embodiments, the human is older than 45 years, 50 years, older than 55 years, older than 60 years, older than 65 years, older than 70 years, older than 75 years or older than 80 years.

6.5.6 Use in the Treatment of Additional Diseases or Symptoms

The therapeutic compositions described herein are useful for alleviating the symptoms of, treating or preventing bladder obstruction, interstitial cystitis, underactive bladder, prostatitis, bladder and prostate inflammation, prostate fibrosis or pelvic pain. The alleviation of symptoms of these diseases or conditions can be manifested by comparison to the same subject prior to administration or treatment with the therapeutic composition. The subject can be a human, for example a male or a female. In some embodiments, the human is older than 45 years, older than 50 years, older than 55 years, older than 60 years, older than 65 years, older than 70 years, older than 75 years or older than 80 years.

7. EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

7.1 Example 1

Preparation of Therapeutic Composition Using Cranberry Seed Meal

Therapeutic compositions described herein can be made as follows. Cranberry berries, skins, juice or pomace are weighed and mixed to create a slurry. If the composition is enriched in cranberry seeds, seeds are added to the slurry. Water is added to the slurry to reach about 5%-15% of the solids by weight. The slurry is passed through a 14 mesh screen, a shear pump, spray-dried and milled. If the therapeutic composition is enriched in cranberry seed meal, it is added during the milling. The milled composition is passed through a sieve, sealed and pelletized.

7.2 Example 2

Characterization of the Therapeutic Composition

The therapeutic compositions were prepared as described above and characterized. Table 2 shows the organic acid profile of 5 samples as determined using a modified AOAC (986.13) entitled *Quinic, Malic and Citric Acids in Cranberry Juice Cocktail and Apple Juice*. Analytical column is a C18 reverse phase column with a 5 μm particle size, 25 cm×4.6 mm in tandem with and followed by C18 reverse phase cartridges, with a 5 μm particle size and 10 cm long. Phosphate buffer, 0.2M $KH_2PO_4$, pH 2.4 is used. The elution is isocratic, flow rate 0.80 mL/min, ambient temperature and wavelength 214 nm. The method was originally written for cranberry juice and adapted for powders, where a dilution of the test agent was performed in the mobile phase. CAS # for the standard are as follow: CAS-77-92-9 (citric acid), CAS-6915-15-7 (malic acid), CAS-77-95-2 (quinic acid). The formula used to calculate the concentration of each organic acid is as follow: (PA/PA')×(V'/V)×C, where PA and PA'=peak area of test solution and standard, respectively; V and V'=volume of test solution and standard, respectively; and C=concentration of standard, %. The results are presented in Table 2 below.

TABLE 2

| Sample | Quinic Acid (%) | Malic Acid (%) | Citric Acid (%) | Total (%) |
|---|---|---|---|---|
| 1 | 2.43 | 1.54 | 2.38 | 6.35 |
| 2 | 2.31 | 0.93 | 1.94 | 5.18 |
| 3 | 2.99 | 1.43 | 2.99 | 7.41 |
| 4 | 2.40 | 1.36 | 2.15 | 5.91 |
| 5 | 2.75 | 1.65 | 3.00 | 7.40 |
| Mean ± SD | 2.58 ± 0.28 | 1.38 ± 0.28 | 2.49 ± 0.48 | 6.45 ± 0.97 |

Table 3 shows the sugar content of 5 samples as determined by HPLC, using a modification of AOAC method AOAC 977.20. The column used is a 300×4 (id) mm μ-Bondapak/Carbohydrate (Waters Associates, No. 84038) with a guard column. The mobile phase consists of non-spectro acetonitrile diluted with water (83/17, v/v). The sugar standard solution consisted of fructose (CAS #57-48-7), glucose (CAS #50-99-7) and sucrose (CAS #57-50-1). The sample was diluted in water and filtered through a 45 μm filter. 10 μL of sample are injected to the column at room temperature. The flow rate is 1.0 mL/min under isocratic conditions for 20 min. A refractive index detector is used. Glucose, fructose, and sucrose are calculated from integrator values or from peak heights as follows: Weight % sugar=100×(PH/PH')×(V/V')×(W'/W) where PH and PH'=peak heights (or integrator values) of sample and standard, respectively; V and V'=mL sample and standard (50 and 100) solutions, respectively; and W and W'=g sample (5.000) and standard, respectively. The results are presented in Table 3 below.

TABLE 3

| Sample | Sugar Content (g/100 g) |
|---|---|
| 6 | 8.7 |
| 7 | 4.0 |
| 8 | 7.7 |
| 9 | 5.9 |
| 10 | 7.3 |
| Mean ± SD | 6.7 ± 1.8 |

Concentration of proanthocyanidins was analyzed by HPLC-fluorescence using a Develosil Diol or equivalent. The column size is 250 mm×4.6 mm with a 5 micron particle size. The column compartment is maintained at 35° C. The solvents used are as follows: (A) 2% acetic acid in acetonitrile and (B) is 95:3:2 methanol/water/acetic acid. A linear gradient was used from 0% to 40% B, in 35 min; 40% to 100% B, in 40 min; 100% isocratic B, in 45 min; and 100% to 0% B, in 50 min.

The anthocyanins (peonidin-3-galactoside, peonidin-3-glucoside, peonidin-3-arabinoside, cyanidin-3-glucoside, cyanidin-3-galactoside, cyanidin-3-arabinoside) are analyzed by HPLC-UV at a wavelength of 535 nm. The column is Synergi Hydro-RP 250 mm×4, 6 mm with a 4 μm particle size. The column compartment is maintained at room temperature. The mobile phase A consists of an aqueous 5% formic acid solution and mobile phase B of methanol. The gradient applied is 0-2 min, 5% B; 2-10 min, 5-20% B; 10-15 min, 20% B; 15-30 min, 20-25% B; 30-35 min, 25% B; 35-50 min, 25-33% B; 50-55 min, 33% B; 55-65 min, 33-36% B; 65-70 min, 36-45% B; 70-75 min, 45-53% B; 75-80 min, 53-55% B; 80-84 min, 55-70% B; 84-88 min, 70-5% B; 88-90 min, 5% B.

The rest of the phenolics are analyzed by UPLC-MS/MS using the following method. An Acquity T3 column (150 mm×2.1 mm id, 1.8 μm particle size) from Waters Associates is used and placed in the UPLC column compartment maintained at a temperature of 30° C. The solvents used are 0.1% Formic acid (A) and acetonitrile (B). A linear gradient is applied from 5% B; 0-4.5 min, 5-20% B; 4.5-6.45 min, isocratic 20% B; 6.45-13.5 min, 20-45% B; 13.5-16.5 min 45-100% B; 16.5-19.5 min isocratic 100% B; 19.5-19.52 min 100-5% B; 19.52-22.5 min. The detection was done by MS/MS and all standard compounds were tuned individually. The results are shown in Table 4.

TABLE 4

| Class | Subclass | Phytochemical | Concentration (mg/100 g) |
|---|---|---|---|
| Flavonoids | Flavan-3-ols | Proanthocyanidins | 1078.9* |
| | Flavonols | Quercetin | 176.6 |
| | | Quercetin-3-glucoside | 83.2 |
| | | Quercetin-3-rhamnoside | 34.2 |

TABLE 4-continued

| Class | Subclass | Phytochemical | Concentration (mg/100 g) |
|---|---|---|---|
| | | Quercetin-3-xyloside | 21.9 |
| | | Quercetin-3-arabinoside | 30.2 |
| | | Myricetin | 11.8 |
| | Anthocyanin | Peonidin-3-galactoside | 27.2 |
| | | Peonidin-3-glucoside | 2.9 |
| | | Peonidin-3-arabinoside | 14.3 |
| | | Cyanidin-3-glucoside | 1.1 |
| | | Cyanidin-3-galactoside | 22.5 |
| | | Cyanidin-3-arabinoside | 17.7 |
| Phenolic acids | Hydroxybenzoic | Protocatechuic acid | 21.7 |
| | Hydroxycinnamic acid | p-Coumaric acid | 51.7 |
| | | Caffeoyl-glucoside | 21.2 |
| | | Coumaroyl-glucoside | 10.7 |
| | | Cafeic acid | 14.3 |
| | | Chlorogenic acid | 33.8 |

*Measured by UPLC-MS/MS.

Proanthocyanidin levels are typically >0.3% when measured using the BL-DMAC method (Prior et al., "Multi-laboratory validation of a standard method for quantifying proanthocyanidins in cranberry powders" *J Sci Food Agric.* 90:1473-8 (2010)), >1.5% when measured using a modified HPLC method in which catechin monomers (quantified by HPLC-UV) are subtracted from total polyphenols measured by folin (Sakakibara et al., "Simultaneous Determination of All Polyphenols in Vegetables, Fruits and Teas" *J. Agri. Food. Chem.*, Vol. 51. Pp 572-580 (2003); *Methods in Enzymology*, Volume 299, "Oxidants and Antioxidants Part A" Pages 152-178, 1999 (modified)), or >5% when using a modified European Pharmacopeia method (European Pharmacopoeia 6.0; 01/2008:1220), and >1% by HPLC-fluorescence.

Lignans are analyzed by UPLC-MS/MS using a 2.1 mm×150 mm ACQUITY BEH C18 reverse phase 1.7 μm particle size column. The column compartment was maintained at 30° C. The solvents used are (A) Formic acid 0.1% and (B) Acetonitrile. The gradient is 5% B, 8.0 min, 30% B, 9.0 min, 30% B, 10.0 min, 50% B, 12.0 min, 50% B, 15.0 min, 95% B, 17.0 min 95% B, 17.5 min, 5% B, 23.0 min, 5% B. The detection was done by MS/MS and all standard compounds were tuned individually. The results are shown in Table 5.

TABLE 5

| Name | Concentration (μg/100 g) |
|---|---|
| Lariciresinol | 51.3 |
| Lariciresinol-sesquilignan | 3.8 |
| Secoisolariciresinol | 12.0 |
| Pinoresinol | 77.8 |

7.3 Example 3

Determination of Efficacy of Therapeutic Compositions Against LUTS

The therapeutic composition supplied by NATUREX-DBS LLC., USA, was used. Capsules consisted of either 500 mg of the therapeutic composition, or a combination of 250 mg of the therapeutic composition and 250 mg of placebo, or 500 mg of placebo. The composition of the placebo was as follows: low density STAR-DRI® 1015A maltodextrin, canola oil, Red 40 Lake, sodium aluminum silicate and Blue 1 Lake. The capsules were indistinguishable in appearance. All capsules were provided in identical plastic boxes with safe seal.

The study was a 6-month, single-center, randomized, double-blind, placebo controlled trial, consisting of three parallel treatment arms. Inclusion criteria comprised of: IPSS score between 8 to 19, individuals older than 45 years old and prostate specific antigen (PSA) values lower than 2.5 ng/mL. Exclusion criteria included food allergies, recent prostatitis, chronic liver or kidney diseases, as well as neurological, gastrointestinal or metabolic disorder or any other chronic health condition such as diabetes, excess consumption of caffeine or alcohol. Subjects were also ineligible if they had prior invasive treatment for BPH, recent treatment with α-blockers (within 1 month) or 5α-reductase inhibitors (within 6 months), phytotherapy including saw palmetto, beta-sitosterol, pygeum or other complementary therapy (within 3 months). The primary outcome measure was the IPSS, evaluated at baseline, 3 and 6 months. Secondary outcome measures included quality of life (QoL) at baseline, 3 and 6 months, as well as bladder voided volume (Vol), maximum urinary flow rate (Qmax), average urinary flow rate (Qave) and ultrasound estimated post-void residual urine volume (PVR), serum PSA, selenium, interleukin-6 (IL-6) and C-reactive protein (CRP), at baseline and 6 months.

Participants were randomly assigned to consume daily 500 mg of the therapeutic composition (n=40), 250 mg of the therapeutic composition (n=43) or placebo (n=41) for 6 months. The randomization plan for treatment assignment to subjects was generated with on line software QuickCalcs (GraphPad Software Inc., USA, last accessed on Jul. 2, 2014) and carried out by study staff.

Participants were observed at baseline, on day-90 (3-month) and day-180 (6-month). During the health examination on the first day, and day-180 the following actions were required and health parameters were assessed: (i) detailed medical history, (ii) assessment of all concurrent medical drugs and therapies, (iii) dietary habits, (iv) completion of the IPSS questionnaire, including a question on QoL, (v) urinanalysis, (vi) uroflowmetry, (vii) kidney and bladder ultrasound and (viii) a blood laboratory analysis including PSA. On day-90, only the physical examination and IPSS score were performed. The therapeutic composition bottles were collected at day-90 and at the end of study. Compliance was assessed by performing remaining capsule counts.

Uroflowmetry data: Qmax and Qave were measured using FlowMic (Medkonsult, Czech Republic). The subjects were instructed not to urinate for several hours before the test and to drink at least 1 L of fluids to ensure a full bladder. The Qmax and Qave were calculated by measuring the Vol per unit of time. PVR was assessed using an ultrasound device BK Medical Viking 2400 with abdominal probe 3-7 MHz. Vol and PVR were calculated using the formula for a prolate ellipsoid (width×length×height×0.523). Qmax, Qave, Vol and PVR were measured on day-0 and day-180.

Basic biochemical and hematological parameters were determined in all samples using a HITACHI Modular Evo P analyzer (Hitachi, Japan). Serum PSA was determined using an Architect type LEIA analyzer (Abbott Laboratories, Abbott Park, Ill., USA). CRP was determined by a Quikread 101 and IL-6 by the system Modular® Analytics. Selenium in plasma was estimated by atomic absorption spectrometry using the AA6300 instrument (Shimadzu, Japan). Hemoglobin (Hb), hematocrit (Htc), erythrocytes (RBC), thrombocytes (PLT) and leukocytes (WBC) were measured in $Na_2EDTA$ blood.

The data of the treatment groups was compared with respect to baseline measures using the Wilcoxon matched paired test. The primary and secondary analyses were based on the per protocol population that included all eligible participants who were treated during the entire length of the study. A Mann-Whitney U test was used to compare both treatment dose to placebo data. P-values <0.05 were considered to be significant.

An analysis of covariance was used to test whether there was an effect of the dose on the outcome measure at the end of treatment. This analysis of covariance used the daily dose units of 250 mg as a continuous variable and the baseline measurements of the outcome as a covariate. Box plots of residuals were examined against dose (0, 250, 500 mg) to determine whether the residuals were bell-shaped and whether there was an indication of a non-linear dose effect.

PVR was considered to follow a two-stage process because some proportion of participants had no measurable PVR. This proportion was modelled as a binomial distribution. The volume of urine among participants with PVR was modelled using a truncated Poisson distribution. This two stage model was fit using the hurdle function in the 'pscl' package (Stanford University) running on R version 3.0.0. Dose/250 mg, baseline PVR and baseline IPSS were entered into this model.

A total of 148 men were pre-screened for the study. FIG. 1 provides a CONSORT diagram of the 148 men attending the first screening visit. A total of 124 men were randomized, 41 to the placebo group, 43 to the therapeutic composition 250 mg group and 40 to the therapeutic composition 500 mg group. In the therapeutic composition 500 mg group, 2 participants were lost to follow-up and were not included in the per protocol analysis.

Table 6 presents a summary of baseline characteristics and LUT function measures across the three groups of the analysis. Results are presented as mean±standard deviation (SD).

TABLE 6

| | Placebo (n = 41) | Therapeutic Composition 250 mg (n = 43) | Therapetic Composition 500 mg (n = 38) |
|---|---|---|---|
| Age (years) | 54.0 ± 5.1 | 53.3 ± 5.2 | 52.5 ± 5.4 |
| Weight (kg) | 89.3 ± 11.9 | 91.2 ± 11.9 | 90.1 ± 8.0 |
| Height (cm) | 178.5 ± 6.6 | 180.6 ± 6.6 | 180.7 ± 6.2 |
| Body Mass Index | 28.1 ± 3.8 | 27.9 ± 2.9 | 27.7 ± 3.0 |
| Systolic Blood Pressure (mmHg) | 131.1 ± 12.1 | 130.6 ± 10.1 | 132.1 ± 11.5 |
| Diastolic Blood Pressure (mmHg) | 80.1 ± 7.3 | 80.5 ± 7.2 | 80.9 ± 7.4 |
| Heart Beat (bpm) | 68.9 ± 3.5 | 67.8 ± 4.6 | 68.1 ± 4.4 |
| IPSS (score) | 9.1 ± 2.0 | 9.7 ± 3.1 | 9.4 ± 2.0 |
| PVR (mL) | 15.0 ± 19.2 | 15.9 ± 23.2 | 17.8 ± 21.0 |
| $Q_{max}$ (mL/sec) | 22.0 ± 7.8 | 20.5 ± 7.1 | 19.5 ± 7.5 |
| $Q_{ave}$ (mL/sec) | 14.3 ± 5.2 | 12.5 ± 4.6 | 12.5 ± 5.5 |
| Bladder Volume (mL) | 408.5 ± 117.9 | 339.9 ± 114.4 | 339.0 ± 118.9 |

Participants had a mean age of 53.3±5.4 years with a mean IPSS score of 9.4±2.4. Adherence with scheduled visits was 98.4%. Compliance to the treatment was 100%. IPSS data with voiding and storage symptom subscore and QoL data during the 6-month treatment period are presented in Table 7. The voiding and storage subscores corresponded to questions 1 (incomplete emptying), 3 (intermittency), 5 (weak stream), 6 (straining) and questions 2 (frequency), 4 (urgency), 7 (nocturia), respectively. There was a decrease in IPSS score in the groups taking the therapeutic composition at 250 mg and at 500 mg at the end of the 6-month period with a significant difference versus placebo (p=0.05 and p<0.001, respectively using a Mann-Whitney U test).

Participants IPSS score, voiding and storage symptom score and quality of life score at baseline (Day-0), 3 months (Day-90) and 6 months (Day-180) after placebo, the therapeutic composition at 250 mg or 500 mg intake are shown in Table 7 and Table 8. In Table 7, results are presented as mean±SD and as median along with first and third quartiles.

TABLE 7

| | Group | Day-0 Mean ± SD Median (1st and 3rd quartile) | | Day-90 | | Day-180 | p-value* | % change at day-180 |
|---|---|---|---|---|---|---|---|---|
| Total IPSS score | Placebo | 9.1 ± 2.0<br>8.0 (8.0-9.0) | | 7.4 ± 2.0<br>7.0 (6.0-8.0) | | 7.6 ± 2.6<br>8.0 (6.0-9.0) | | 0% |
| | Therapeutic composition 250 mg | 9.7 ± 3.1<br>8.0 (8.0-10.0) | 0.63 | 7.6 ± 3.7<br>7.0 (5.0-10.0) | 0.60 | 6.6 ± 3.4<br>6.0 (5.0-8.0) | 0.05 | −25% |
| | Therapeutic composition 500 mg | 9.4 ± 2.0<br>9.0 (8.0-10.0) | 0.26 | 6.5 ± 2.6<br>7.0 (4.0-8.0) | 0.11 | 5.3 ± 2.5<br>5.0 (4.0-7.0) | <0.001* | −44% |
| Voiding/obstructive symptoms score | Placebo | 4.9 ± 1.8<br>5.0 (3.75-5.0) | | 5.1 ± 2.4<br>4.0 (4.0-6.0) | | 4.6 ± 1.8<br>4.0 (3.0-6.0) | | −20% |
| | Therapeutic composition 250 mg | 3.7 ± 1.7<br>3.0 (3.0-5.0) | 0.89 | 3.6 ± 2.7<br>3.0 (2.0-5.0) | 0.44 | 2.9 ± 1.7<br>3.0 (2.0-4.0) | 0.18 | 0% |
| | Therapeutic composition 500 mg | 3.8 ± 2.4<br>4.0 (2.0-5.25) | 0.55 | 3.4 ± 2.8<br>3.0 (1.0-5.0) | 0.03* | 2.3 ± 1.4<br>2.0 (1.0-3.0) | <0.001* | −50% |
| Storage/irritative symptoms score | Placebo | 4.2 ± 1.3<br>4.0 (3.75-5.0) | | 4.6 ± 1.5<br>4.0 (4.0-5.75) | | 4.8 ± 1.6<br>4.5 (4.0-6.0) | | +13% |
| | Therapeutic composition 250 mg | 3.7 ± 1.4<br>4.0 (3.0-4.25) | 0.27 | 3.8 ± 1.8<br>4.0 (2.0-4.75) | 0.72 | 3.6 ± 2.0<br>3.5 (2.0-5.0) | 0.13 | −13% |
| | Therapeutic composition 500 mg | 3.7 ± 1.4<br>4.0 (3.0-5.0) | 0.18 | 3.3 ± 1.5<br>3.0 (2.0-4.0) | 0.61 | 3.0 ± 2.0<br>3.0 (2.0-4.0) | 0.018* | −25% |

TABLE 7-continued

| | Group | Day-0<br>Mean ± SD Median<br>($1^{st}$ and $3^{rd}$ quartile) | | Day-90 | | Day-180<br>p-value* | | % change at<br>day-180 |
|---|---|---|---|---|---|---|---|---|
| Quality of Life | Placebo | 2.4 ± 0.9<br>2.0 (2.0-3.0) | | 2.1 ± 0.8<br>2.0 (2.0-2.0) | | 1.9 ± 0.7<br>2.0 (1.75-2.0) | | 0% |
| | Therapeutic composition 250 mg | 2.4 ± 0.8<br>2.0 (2.0-3.0) | 0.64 | 2.2 ± 0.9<br>2.0 (2.0-3.0) | 0.52 | 2.0 ± 0.7<br>2.0 (2.0-2.0) | 0.71 | 0% |
| | Therapeutic composition 500 mg | 2.1 ± 0.7<br>2.0 (2.0-2.0) | 0.03 | 2.0 ± 0.7<br>2.0 (2.0-2.0) | 0.72 | 1.9 ± 0.5<br>2.0 (2.0-2.0) | 0.63 | 0% |

*Denotes a significant difference versus placebo using the Mann-Whitney U test at each individual time point (p < 0.05).

In Table 8, results represent the mean±Standard Error of the Mean (SEM).

TABLE 8

| Group | Day-0<br>IPSS Total<br>Mean ± SEM | Day-90<br>IPSS Change<br>versus baseline<br>Mean ± SEM | Day-180<br>IPSS Change<br>versus baseline<br>Mean ± SEM |
|---|---|---|---|
| Placebo | 9.1 ± 0.3 | −1.71 ± 0.36 | −1.54 ± 0.33 |
| Therapeutic Composition 250 mg | 9.7 ± 0.5 | −2.16 ± 0.38 | −3.09 ± 0.46* |
| Therapeutic Composition 500 mg | 9.4 ± 0.3 | −2.89 ± 0.36* | −4.08 ± 0.31* |

*Denotes a significant difference versus placebo using the Mann-Whitney U test at each individual time point (p < 0.05).

The mean difference in IPSS between baseline, 3-month and 6-month for the three groups is plotted in FIG. 2. Data points represent the mean difference±the standard error of the mean. Asterisk indicates p<0.05 versus placebo based on analysis of covariance at the end of treatment. At 6-month, mean difference and corresponding 95% confidence interval (CI) were −1.5 (−2.2, −0.89) for the placebo group, −3.1 (−4.0, −2.2) for the therapeutic composition 250 mg group, and −4.1 (−4.7, −3.5) for the therapeutic composition 500 mg group.

Analysis of covariance for IPSS at 6-month with baseline IPSS entered as a covariate showed a significant dose effect (t119=−4.8, p<0.0001) and a significant effect of baseline score (t119=8.3, p<0.0001).

IPSS voiding subscore was significantly decreased when compared to placebo in the therapeutic composition 500 mg group 3 months after initiation of the treatment and up to 6 months (p=0.03 and p<0.001, respectively), while the IPSS storage subscore was significantly decreased versus placebo only at the end of the study (p=0.018). There was no statistically significant improvement in the IPSS storage subscore in the group treated with therapeutic composition at 250 mg. There was no change in the QoL questionnaire for both doses.

There was a significant improvement in all uroflowmetry parameters studied versus baseline at the end of the intervention with therapeutic composition at the 500 mg dose (p<0.05). Table 9 shows LUT function measurements at baseline (Day-0) and 6 months (Day-180) after placebo, therapeutic composition at 250 mg or 500 mg. Results in Table 9 are presented as mean±SD.

TABLE 9

| | | $Q_{max}$, mL/s | $Q_{ave}$, mL/s | PVR, mL | Vol, mL |
|---|---|---|---|---|---|
| Placebo | Day-0 | 22.0 ± 7.8 | 14.3 ± 5.2 | 15.0 ± 19.2 | 408.5 ± 117.9 |
| | Day-180 | 21.9 ± 8.6 | 14.2 ± 5.1 | 14.4 ± 18.3 | 364.3 ± 112.5 |
| | p-value | 0.424 | 0.722 | 0.956 | 0.004 |
| Therapeutic composition 250 mg | Day-0 | 20.5 ± 7.1 | 12.5 ± 4.6 | 15.9 ± 23.2 | 339.9 ± 114.4 |
| | Day-180 | 21.4 ± 6.7 | 13.2 ± 4.0 | 13.6 ± 18.1 | 368.6 ± 104.6 |
| | p-value | 0.191 | 0.107 | 0.588 | 0.279 |
| Therapeutic composition 500 mg | Day-0 | 19.5 ± 7.5 | 12.5 ± 5.4 | 17.8 ± 21.0 | 339.0 ± 118.9 |
| | Day-180 | 21.7 ± 8.9 | 13.8 ± 5.7 | 9.9 ± 13.6 | 393.0 ± 134.0 |
| | p-value | 0.018* | 0.040* | 0.027* | 0.014* |

*Denotes a significant difference versus baseline using the Wilcoxon Matched-Pairs test.

Further analysis was performed to evaluate whether there was a dose-response effect at the end of the intervention and whether the data could be adjusted based on baseline data. A large proportion of participants reported no measurable PVR (17/41 for 0 mg dose; 22/43 for the 250 mg dose; and 19/38 for the 500 mg dose). While existence of a non-zero PVR was nominally lower in the 250 and 500 mg groups, no dose effect was found. Given the existence of residual volume however, that volume was significantly associated with dose ($z=-3.0$, $p=0.003$). This model indicates that among participants with non-zero PVR, residual urine volume would be expected to decrease by a factor of 0.09 (95% CI: 0.03-0.14) for every 250 mg increase in dose, for a given baseline PVR and IPSS.

Clinical hematology parameters, which were within normal range at the beginning and at the end of the study, thereby demonstrating the safety of the intervention product.

This double-blind, randomized, placebo controlled study demonstrated the efficacy and the safety of the daily intake of the therapeutic composition at 250 or 500 mg in men with LUTS for 6 months. At the end of the study, the decrease in IPSS score was significant and dose dependent (−3.1 and −4.1 in the 250 mg and 500 mg groups, $p=0.05$ and $p<0.001$, respectively) versus the placebo group (−1.5), while no side effects were observed.

What is claimed is:

1. A solid oral dosage form comprising about 250 mg to about 500 mg of a therapeutic composition for treating or alleviating lower urinary tract symptoms (LUTS), wherein the therapeutic composition comprises dried cranberry powder and is enriched in cranberry seeds or cranberry seed meal,
   wherein the cranberry seeds or cranberry seed meal are present in the therapeutic composition in an amount of about 15% to about 25% by weight of the dried cranberry powder,
   wherein the therapeutic composition comprises about 5% to 12% or organic acids by weight,
   wherein the therapeutic composition of 250 to 500 mg provides an amount of organic acids of less than about 12.5 to 60 mg, an amount of anthocyanins of less than about 0.175 mg to 0.75 mg, an amount of proanthocyanidins of less than about 0.5 mg to 7.5 mg, and an amount of total phenolics of less than about 4.25 mg to 16.25 mg, and
   wherein the solid oral dosage form is a tablet, a capsule, a softgel, a powder, or a granule.

2. The solid oral dosage of claim 1, wherein the cranberry is *Vaccinium macrocarpon*.

3. The solid dosage form of claim 1, wherein the cranberry is *Vaccinium microcarpon*.

4. The solid dosage form of claim 1, wherein the cranberry is *Vaccinium oxycoccus*.

5. The solid dosage form of claim 1, wherein the cranberry seeds or cranberry seed meal are present in the composition in an amount of about 20% by weight of the dried cranberry powder.

6. The solid dosage of claim 1, wherein the composition comprises less than 10% of organic acids by weight.

7. The solid dosage form of claim 1, wherein the composition comprises less than about 15% of sugars by weight.

8. The solid dosage form of claim 1, wherein the composition comprises from about 1% to about 5% of quinic acid by weight.

9. The solid dosage form of claim 8, wherein the composition comprises from about 2.2% to about 3.2% of quinic acid by weight.

10. The solid dosage form of claim 1, wherein the composition comprises from about 0.4% to about 4% of malic acid by weight.

11. The solid dosage form of claim 10, wherein the composition comprises from about 0.8% to about 1.8% of malic acid by weight.

12. The solid dosage form of claim 1, wherein the composition comprises from about 1% to about 5% of citric acid by weight.

13. The solid dosage form of claim 12, wherein the composition comprises from about 1.8% to about 3.2% of citric acid by weight.

14. The solid dosage form of claim 1, wherein the composition comprises:
    0.5% to 5.0% proanthocyanidins, 0.05% to 1.5% quercetin, 0.001% to 0.1% quercetin-3-glucoside, 0.001% to 0.1% quercetin-3-rhamnoside, 0.001% to 0.1% quercetin-3-xyloside, 0.001% to 0.1% quercetin-3-arabinoside, 0.001% to 0.5% myricetin, 0.001% to 0.1% peonidin-3-galactoside, 0.001% to 0.1% peonidin-3-glucoside, 0.001% to 0.1% peonidin-3-arabinoside, 0.001% to 0.1% cyanidin-3-glucoside, 0.001% to 0.1% cyanidin-3-galactoside, 0.001% to 0.1% cyanidin-3-arabinoside, 0.001% to 0.1% protocatechuic acid 0.001% to 0.1% p-coumaric acid, 0.001% to 0.1% caffeoyl-glucoside, 0.001% to 0.1% coumaroyl-glucoside, 0.001% to 0.1% cafeic acid, 0.001% to 0.1% chlorogenic acid or 0.01 to 1.5% ursolic acid by weight.

15. The solid dosage form of claim 14, wherein the composition comprises:
    1.0% to 1.2% proanthocyanidins, 0.16% to 0.20% quercetin, 0.07% to 0.09% quercetin-3-glucoside, 0.03% to 0.04% quercetin-3-rhamnoside, 0.019% to 0.025% quercetin-3-xyloside, 0.025% to 0.035% quercetin-3-arabinoside, 0.010% to 0.014% myricetin, 0.022% to 0.030% peonidin-3-galactoside, 0.0025% to 0.0035% peonidin-3-glucoside, 0.010% to 0.020% peonidin-3-arabinoside, 0.0005% to 0.0015% cyanidin-3-glucoside, 0.015% to 0.030% cyanidin-3-galactoside, 0.010% to 0.025% cyanidin-3-arabinoside, 0.019% to 0.025% protocatechuic acid, 0.04% to 0.06% p-coumaric acid, 0.015% to 0.025% caffeoyl-glucoside, 0.005% to 0.015% coumaroyl-glucoside, 0.010% to 0.015% cafeic acid or 0.030% to 0.04% chlorogenic acid by weight.

16. The solid dosage form of claim 1, wherein the composition comprises 1 to 100 μg lariciresinol, 1 to 100 μg secoisolariciresinol or 1 to 100 μg pinoresinol per 100 g of the composition by weight.

17. The solid dosage form of claim 16, wherein the composition comprises about 51 μg lariciresinol, about 12 μg secoisolariciresinol or about 78 μg pinoresinol per 100 g of the composition by weight.

18. The solid dosage form of claim 1, comprising about 250 mg of the therapeutic composition.

19. The solid dosage form of claim 1, comprising about 500 mg of the therapeutic composition.

* * * * *